United States Patent
Bennett

(10) Patent No.: US 6,699,174 B1
(45) Date of Patent: Mar. 2, 2004

(54) FEMALE URINARY INCONTINENCE DEVICE

(76) Inventor: Patricia A. Bennett, 1300 J.E. Woody Rd., Springtown, TX (US) 78082

( * ) Notice: Subject to any disclaimer, the term of this patent is extended or adjusted under 35 U.S.C. 154(b) by 0 days.

(21) Appl. No.: 09/888,010

(22) Filed: Jun. 22, 2001

Related U.S. Application Data

(60) Provisional application No. 60/262,330, filed on Jan. 18, 2001.

(51) Int. Cl.$^7$ .................................................. A61F 2/00
(52) U.S. Cl. ......................... 600/29; 604/319; 604/321; 604/326; 604/329; 4/144.2; 4/144.3; 600/32
(58) Field of Search ................................ 604/319, 321, 604/322, 326, 329, 331, 334, 338, 339, 340, 341, 352; 600/32, 29, 31; 4/144.1, 144.2, 144.3, 144.4

(56) References Cited

U.S. PATENT DOCUMENTS

| | | | |
|---|---|---|---|
| 3,554,184 A | 1/1971 | Habib | 128/1 |
| 3,661,155 A | 5/1972 | Lindan | 128/295 |
| 3,705,575 A | 12/1972 | Edwards | 128/1 R |
| 4,139,006 A | 2/1979 | Corey | 128/127 |
| 4,681,572 A * | 7/1987 | Tokarz et al. | 604/329 |
| 4,784,654 A * | 11/1988 | Beecher | 604/329 |
| 4,795,449 A * | 1/1989 | Schneider et al. | 604/329 |
| 4,875,898 A | 10/1989 | Eakin | 604/331 |
| 4,889,532 A | 12/1989 | Metz et al. | 604/330 |
| 4,936,838 A * | 6/1990 | Cross et al. | 604/329 |
| 5,002,541 A * | 3/1991 | Conkling et al. | 604/319 |
| 5,049,144 A | 9/1991 | Payton | 604/329 |
| 5,263,947 A | 11/1993 | Kay | 604/331 |
| 5,571,095 A * | 11/1996 | Lu | 604/329 |
| 5,632,736 A * | 5/1997 | Block | 604/329 |
| 5,735,835 A * | 4/1998 | Holland | 604/331 |
| 5,792,042 A | 8/1998 | Cohen et al. | 600/29 |
| 5,887,593 A | 3/1999 | Levius | 128/885 |
| 5,895,349 A | 4/1999 | Tihon | 600/29 |
| 5,908,379 A | 6/1999 | Schaefer et al. | 600/29 |
| 5,976,068 A | 11/1999 | Hakky et al. | 600/29 |

FOREIGN PATENT DOCUMENTS

| | | | | |
|---|---|---|---|---|
| WO | WO9918898 | * | 4/1999 | 604/319 |

* cited by examiner

*Primary Examiner*—Binh Tran
(74) *Attorney, Agent, or Firm*—James E. Walton

(57) ABSTRACT

A female urinary incontinence management device having a base member that adhesively attaches to the patient, and a bag member that is sealingly and releasably attached to the base member. The base member is generally triangular having a top portion that, when attached to the patient, extends across and above the symphysis pubis, side portions that extend down along the groin area, and a short bottom portion that extends across the perineal area. The base member includes an upraised ridge portion into which is integrated a "female" part of a means for sealing the bag member with the base member. The bag member includes a similar upraised ridge portion into which is integrated a "male" part of the means for sealing the bag member with the base member. The bag member may be releasably and sealingly coupled to the base member by interlockingly squeezing the "male" and "female" parts together. In this manner, the bag member may be interchanged several times without having to remove the base member from the patient.

10 Claims, 2 Drawing Sheets

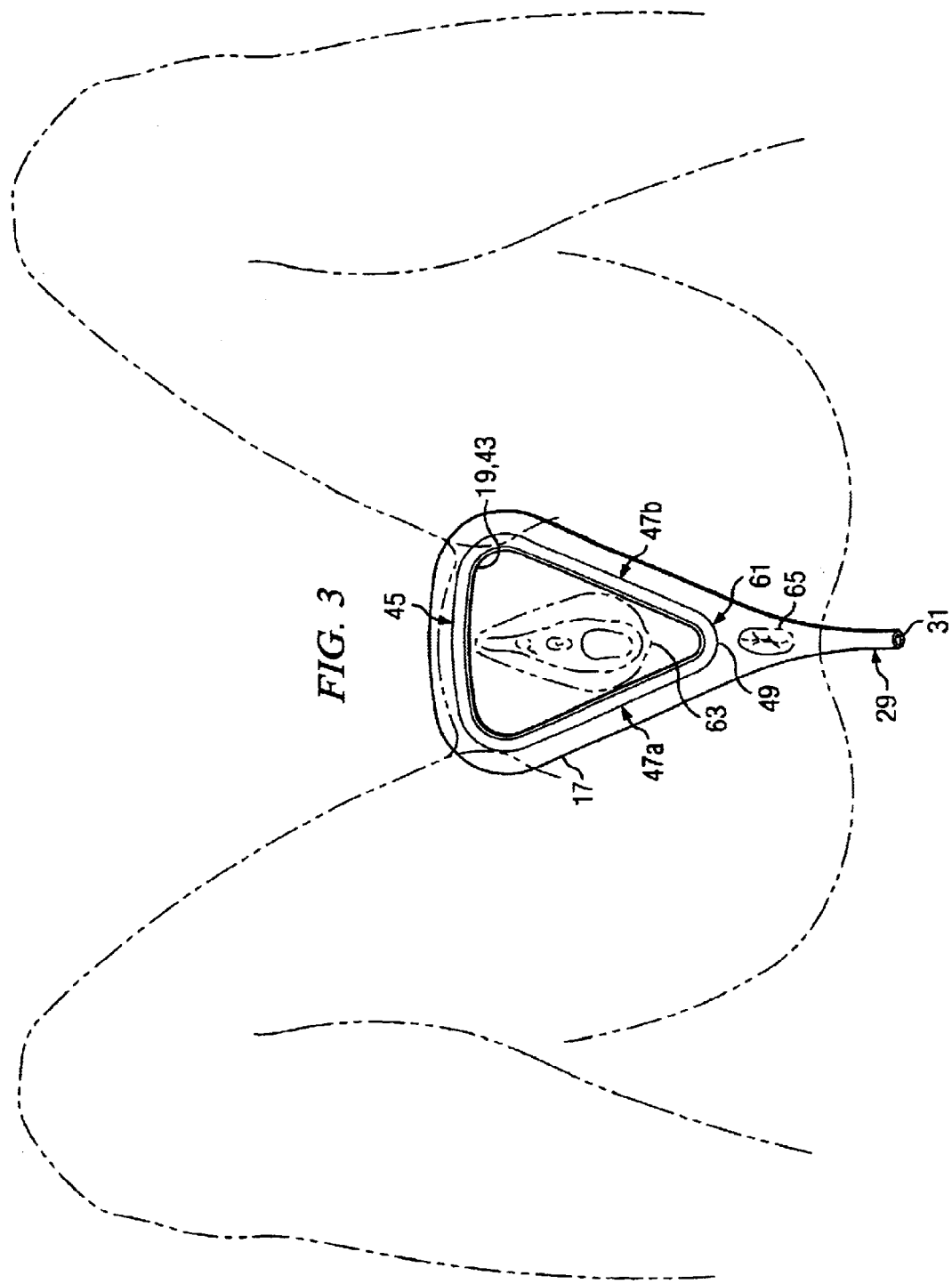

FEMALE URINARY INCONTINENCE DEVICE

This application claims the benefit of U.S. Provisional Application No. 60/262,330, filed Jan. 18, 2001, titled "Female Urinary Incontinence Device."

BACKGROUND ART

1. Field of the Invention

The present invention relates to urinary incontinence devices. In particular, the present invention relates to devices for managing female urinary incontinence.

2. Description of Related Art

Urinary incontinence is believed to affect 15% to 30% of non-institutionalized people over the age of 60, and over 50% of the people in convalescent and nursing homes. Treatment for urinary incontinence generally falls into the following categories: (1) management devices, which either restrict the flow of urine, or simply redirect and retain the urine; (2) behavioral treatment, which involves bladder re-training by voiding on a timed schedule or the performance of exercises to strengthen pelvic muscles; (3) pharmacological treatment, which involves the long-term use of drugs; and (4) surgical treatment, which involves the performance of major surgery while the patient is under anesthesia. Although each of these categories of treatment offer some measure of relief, each has significant side effects. The present invention relates to the management of female urinary incontinence.

There are many female urinary incontinence management and control devices on the market at this time, ranging from the most intrusive: urinary tract catheters; to the least intrusive: diapers. Neither of these devices, nor anything in between, offer the safe, comfortable, and non-traumatic control or management of female urinary incontinence. Although urinary tract catheters, such as Foley catheters, are often necessary, their intrusive nature often leads to urinary tract infections. In addition, the insertion and extraction of Foley catheters are quite traumatic for the patient. On the other hand, although diapers are quick and easy to use, and are non-intrusive, they often lead to skin breakdown, and are virtually useless when it is necessary to maintain an accurate measure of a patient's fluid intake and output.

The following U.S. patents represent attempts to manage or control female urinary incontinence: U.S. Pat. No. 3,554,184 to Habib; U.S. Pat. No. 3,661,155 to Lindan; U.S. Pat. No. 3,705,575 to Edwards; U.S. Pat. No. 4,139,006 to Corey; U.S. Pat. No. 4,875,898 to Eakin; U.S. Pat. No. 4,889,532 to Metz et al.; U.S. Pat. No. 5,049,144 to Payton; U.S. Pat. No. 5,263,947 to Kay; U.S. Pat. No. 5,792,042 to Cohen et al.; U.S. Pat. No. 5,887,593 to Levius; U.S. Pat. No. 5,895,349 to Tihon; U.S. Pat. No. 5,908,379 to Schaefer et al.; and 5,976,068 to Hakky et al. All of these devices, with the exception of U.S. Pat. No. 5,263,947 are invasive devices. Not only are invasive devices uncomfortable for the patient, they can cause significant trauma to the patient during insertion and removal. In addition, the risk of urinary tract infection is typically higher with invasive devices.

BRIEF SUMMARY OF THE INVENTION

There is a need for a female urinary incontinence management device that is non-intrusive and that has replaceable components.

Therefore, it is an object of the present invention to provide a female urinary incontinence management device that is non-intrusive and that has replaceable components.

The above objects are achieved by providing a female urinary incontinence management device having a base member that adhesively attaches to the patient, and a bag member that is sealingly and releasably attached to the base member. The base member is generally triangular having a top portion that, when attached to the patient, extends across and above the symphysis pubis, side portions that extend down along the groin area, and a short bottom portion that extends across the perineal area. The base member includes an upraised ridge portion into which is integrated a "female" part of a means for sealing the base member to the bag member. The bag member includes a similar upraised ridge portion into which is integrated a "male" part of the means for sealing the base member to the bag member. The bag member may be releasably and sealingly coupled to the base member by interlockingly squeezing the "male" and "female" parts together. In this manner, the bag member may be interchanged several times without having to remove the base member from the patient.

The present invention has significant advantages, including: (1) it prevents skin breakdown, because urine is prevented from remaining in contact with the skin; (2) it prevents urinary tract infections, because the device is non-intrusive; (3) it improves patient comfort, because the device does not excessively compress the urethra or restrict urine flow; (4) it allows accurate measuring of output of fluids without internal catheterization; and (5) it reduces the number linen changes, resulting in savings in time, cost, and labor.

The above objects and advantages, as well as others, will be evident from the following detailed description of the present invention.

BRIEF DESCRIPTION OF THE DRAWINGS

FIG. 3 is an a perspective view of the female urinary incontinence management device according to the present invention shown applied to a female patient.

DETAILED DESCRIPTION OF THE PREFERRED EMBODIMENT

Figure 1A:
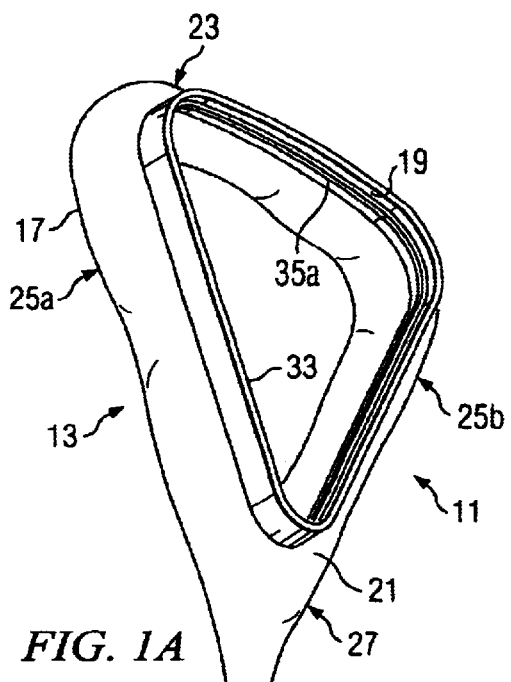
FIG. 1A is a perspective view of a bag member of the female urinary incontinence management device according to the present invention.
Figure 1B:
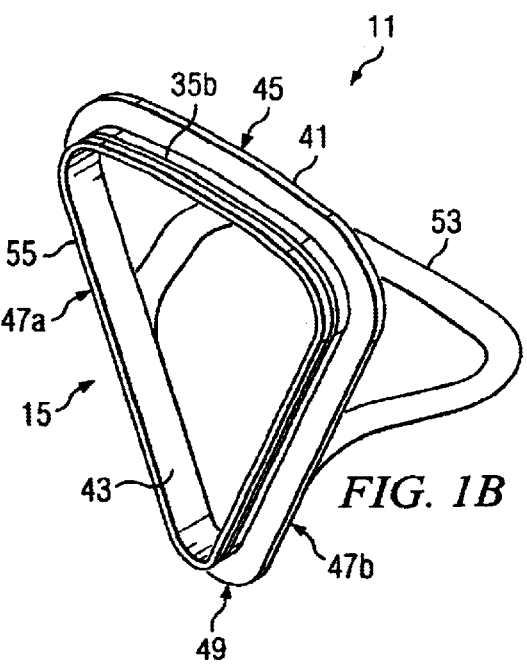
FIG. 1B is a perspective view of a base member of the female urinary incontinence management device according to the present invention.

Referring to FIGS. 1A and 1B in the drawings, the preferred embodiment of a female urinary incontinence management device 11 according to the present invention is illustrated. Device 11 is a non-intrusive, multi-component device for use in managing incontinence in females. Device 11 preferably has a bag member 13, as illustrated in FIG. 1A, and a base member 15, as illustrated in FIG. 1B. Although device 11 is shown only as a two-component device, it should be understood that device 11 may be divided into additional interconnected components for certain applications. In an alternate embodiment of the present invention, bag member 13 and base member 15 may form a single integrated device. Each component of device 11 is preferably made of a flexible, fluid tight material, such as rubber, latex, nylon, or any other material commonly used for such medical devices. As such, each component of device 11 would typically be transparent, or partially transparent. Such transparency allows an attendant to visually inspect device 11 and the fluids within device 11. It should be understood that device 11 may include visual indicia for determining certain data, such as the volume of fluid in or passing through device 11.

Bag member 13 includes a flexible urine collection bag 17 that is generally triangular in shape. Collection bag 17 includes a generally triangular shaped aperture 19 cut into an interior surface 21, which faces the patient. Because aperture 19 is smaller than interior surface 21, collection bag 17 overlaps aperture 19. This overlapping feature provides additional volume within collection bag 17. Collection bag 17 has a wide top portion 23, a pair of side portions 25a and 25b that angle toward each other, and a narrow base portion 27. A drainage tube portion 29 is integral with base portion 27. Drainage tube portion 29 includes an aperture 31 and is configured to be coupled to a conventional urinary drainage tube (not shown) and a conventional urinary drainage bag (not shown).

An upraised ridge portion 33 is integrated into interior surface 21 and completely surrounds aperture 19. Upraised ridge portion 33 extends inward toward the patient. Upraised ridge portion 33 includes a means for releasably sealing bag member 13 to base member 15. Means for releasably sealing bag member 13 to base member 15 may be separated into two parts: one part, such as an interlocking "male" part 35a, may be carried by bag member 13; and the other part, such as an interlocking "female" part 35b, may be carried by base member 15, or vice versa. In the preferred embodiment of the present invention, means 35a and 35b are flexible, interlocking parts that form a fluid tight seal when squeezed together, similar to the widely known and used ZIP-LOCK seal.

Base member 15 includes a flat portion through which an aperture 43 passes to form a generally flat triangular strip 41. Triangular strip 41 has a wide top portion 45, a pair of side portions 47a and 47b that angle toward each other, and a narrow base portion 49. An interior surface 51 (see FIG. 2) of strip 41 faces the patient. Interior surface 51 is coated with a conventional adhesive to allow base member 15 to be sealingly attached to the patient. The adhesive coating is covered and protected by a removable protective strip 53, which is shown in FIGS. 1B and 2 partially removed from interior surface 51.

An upraised ridge portion 55 is integrated into flat triangular strip 41 and completely surrounds aperture 43. Upraised ridge portion 55 extends outward away from the patient. Upraised ridge portion 54 includes a means for releasably sealing bag member 13 to base member 15. As explained above, the female part 35b of the means for releasably sealing bag member 13 to base member 15 is integrated into upraised ridge portion 55.

Figure 2:
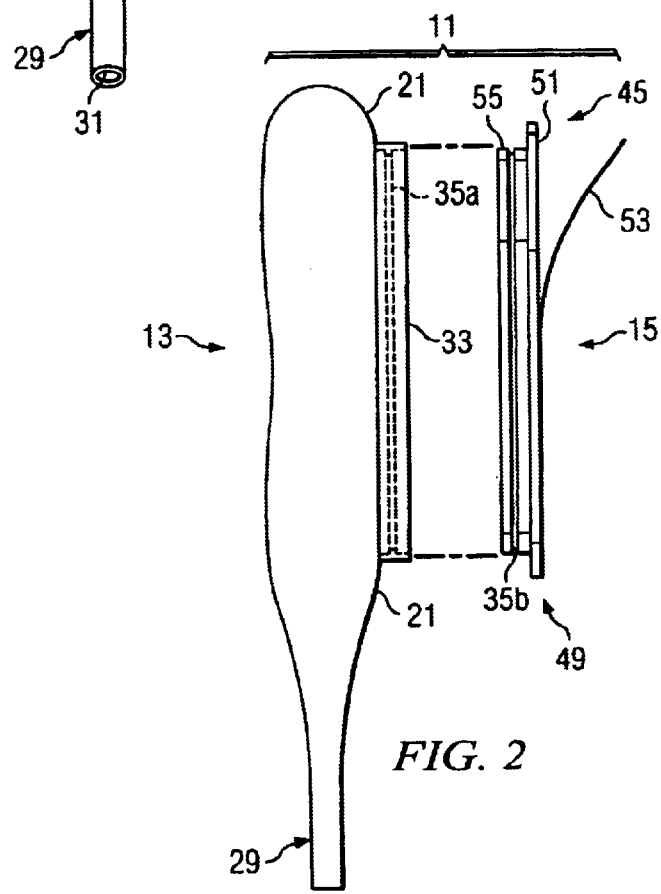
FIG. 2 is a side view of the bag member of FIG. 1A and the base member of FIG. 1B shown side by side prior to being interlocking sealed together.

Referring now to FIG. 2 in the drawings, device 11 is shown in a side view. As is shown, upraised ridge portion 33 of bag member 13 is aligned with upraised ridge portion 55 of base member 15. In this view, bag member 13 and base member 15 have not been interlockingly sealed together. To seal bag member 13 to base member 15, male part 35a and female part 35b are manually aligned and squeezed together to form a fluid tight seal.

Referring now to FIG. 3 in the drawings, device 11 is shown attached to a female patient. The procedure for attaching device 11 to the patient is very simple. First, protective strip 53 is removed from the back of triangular strip 41 of base member 15 to expose the adhesive coating. Triangular strip 41 is then attached to the patient, such that top portion 45 is attached above the symphysis pubis, side portions 47a and 47b are attached along the groin area, and narrow base portion 49 is attached at the perineum 61, between the posterior vulva junction 63 and the anus 65. This forms a fluid tight seal between the patient's skin and base member 15. Then, bag member 13 is releasably sealed to base member 15 by aligning male part 35a and female part 35b and squeezing them together. This forms a fluid tight seal between base member 15 and bag member 13. Finally, a conventional urinary drainage tube and urinary drainage bag or bottle are coupled to device 11 at drainage tube portion 29. After removal, both base member 15 and bag member 13 are properly discarded. It will be appreciated that bag member 13 may be removed and replaced several times before base member needs replacing.

It should be understood that means for releasably sealing bag member 13 to base member 15 may exist in a wide variety of forms. For example, interlocking parts 35a and 35b may be replaced by adhesive layers or strips, clamping mechanisms, sliding mechanisms, chemical mechanisms, or any other mechanism suitable for sealing two parts together.

Device 11 has significant advantages, including: (1) prevention of skin breakdown, because urine is prevented from remaining in contact with the skin; (2) prevention of urinary tract infections, because the device is non-intrusive; (3) improvement of patient comfort, because device 11 does not excessively compress the urethra or restrict urine flow; (4) accurate measurement of output of fluids without internal catheterization; and (5) reduction in the number linen changes, resulting in savings in time, cost, and labor.

It will be appreciated that the present invention may be used in other medical applications. In particular, the present invention may be modified to work in any application in which base member 15 is attached to the patient and bag member 13 is releasably sealed to base member 15 using male part 35a and female part 35b. In these other applications, it will be appreciated that both base member 15 and bag member 13 may be shaped differently, and that bag member 13 may not include an output port, such as urinary tube portion 29, or may include multiple input and output ports for the introduction and removal of fluids from device 11.

For example, the present invention may be adhered to a patient over a wound and used to irrigate the wound. In this example, it will be appreciated that bag member 13 may include one of more fluid input ports for introducing medicine or fluids to the wound, and one or more fluid drainage ports for removing the medicine or fluids from around the wound. Such input and output ports may be similar to urinary tube portion 29, or may include valves to direct and control the flow of the medicine and other fluids. These The present invention is well suited for any medical application in which it is desirable to have one or more components of device 11 releasably sealed to each other.

Although the present invention is shown in a limited number of forms, it is not limited to just these forms, but is amenable to various changes and modifications without departing from the spirit thereof.

I claim:

1. A female urinary incontinence management device comprising:
   a base member having an adhesive surface for attachment to the external tissue surrounding the vulval region of a female;
   a bag member separate from the base member configured for attachment to a urinary drainage tube; and a means for releasably sealing the base member to the bag member.

2. The female urinary incontinence management device according to claim 1, wherein the means for releasably sealing the base member to the bag member is disposed partially on the base member and partially on the bag member.

3. The female urinary incontinence management device according to claim 1, wherein the means for releasably sealing the base member to the bag member is an interlocking zip-type seal in which a male portion is disposed on the base member and a female portion is disposed on the bag member.

4. The female urinary incontinence management device according to claim 1, wherein the means for releasably sealing the base member to the bag member is an interlocking zip-type seal in which a female portion is disposed on the base member and a male portion is disposed on the bag member.

5. The female urinary incontinence management device according to claim 1, wherein the device is non-intrusive.

6. A device for applying fluid to a patient, the device comprising:

a base member having an adhesive surface for attachment to the external tissue surrounding the vulval region of the patient;

a bag member separate from the base member;

a means for releasably sealing the base member to the bag member; and at least one port in fluid communication with the bag member.

7. The device according to claim 6, wherein the means for sealing the base member to the bag member is disposed partially on the base member and partially on the bag member.

8. The device according to claim 6, wherein the means for sealing the base member to the bag member is an interlocking zip-type seal in which a male portion is disposed on the base member and a female portion is disposed on the bag member.

9. The device according to claim 6, wherein the means for sealing the base member to the bag member is an interlocking zip-type seal in which a female portion is disposed on the base member and a male portion is disposed on the bag member.

10. The device according to claim 6, wherein the at least one port in fluid communication with the bag member is an input port for selectively introducing fluid into the bag member; and wherein the device further comprises:

at least one output port in fluid communication with the bag member for selectively removing fluid from the bag portion.

* * * * *